United States Patent
Leussler et al.

(10) Patent No.: US 10,261,144 B2
(45) Date of Patent: Apr. 16, 2019

(54) MAGNETIC RESONANCE IMAGING SYSTEM WITHOUT INTEGRATED BODY COIL

(71) Applicant: KONINKLIJKE PHILIPS N.V., Eindhoven (NL)

(72) Inventors: Christoph Leussler, Eindhoven (NL); Cecilia Possanzini, Eindhoven (NL); Peter Vernickel, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 338 days.

(21) Appl. No.: 14/911,286

(22) PCT Filed: Aug. 15, 2014

(86) PCT No.: PCT/EP2014/067463
§ 371 (c)(1),
(2) Date: Feb. 10, 2016

(87) PCT Pub. No.: WO2015/022416
PCT Pub. Date: Feb. 19, 2015

(65) Prior Publication Data
US 2016/0195594 A1    Jul. 7, 2016

(30) Foreign Application Priority Data
Aug. 15, 2013   (EP) .................................. 13180557

(51) Int. Cl.
*G01R 33/00*   (2006.01)
*G01R 33/34*   (2006.01)
*G01R 33/3415*   (2006.01)
*A61B 5/00*   (2006.01)

(52) U.S. Cl.
CPC ........ *G01R 33/34084* (2013.01); *A61B 5/704* (2013.01); *G01R 33/3415* (2013.01); *G01R 33/34007* (2013.01)

(58) Field of Classification Search
CPC .......... G01R 33/34084; G01R 33/3415; A61B 5/704
See application file for complete search history.

(56) References Cited

U.S. PATENT DOCUMENTS

| 5,477,146 A | 12/1995 | Jones |
| 6,529,004 B1 | 3/2003 | Young |
| 6,591,128 B1 * | 7/2003 | Wu ................. G01R 33/34084 324/318 |
| 2002/0180442 A1 | 12/2002 | Vij |

(Continued)

FOREIGN PATENT DOCUMENTS

| JP | 0268036 H | 3/1990 |
| WO | 2007048032 A1 | 4/2007 |
| WO | 2012063162 A1 | 5/2012 |

*Primary Examiner* — Joseph M Santos Rodriguez

(57) ABSTRACT

A transmit and/or receive coil assembly includes a first and second exchangeable part configured for transmitting and/or receiving RF signals. The exchangeable parts are exchangeable with each other and configured to co-operate with a permanent part of the transmit and/or receive coil assembly during magnetic resonance imaging in order to generate an RF (or B1+) field that covers a volume of interest of the object to be scanned and/or to receive magnetic resonance signals from the volume of interest of the object.

17 Claims, 3 Drawing Sheets

(56) References Cited

U.S. PATENT DOCUMENTS

| | | |
|---|---|---|
| 2004/0135579 A1 | 7/2004 | Takizawa |
| 2008/0238424 A1* | 10/2008 | Possanzini .......... G01R 33/341 324/318 |
| 2009/0027053 A1 | 1/2009 | Decke |
| 2010/0174172 A1* | 7/2010 | Ein-Gal ................ A61B 5/055 600/411 |
| 2011/0031970 A1 | 2/2011 | Nimomiya |
| 2012/0153954 A1 | 6/2012 | Ota et al. |
| 2012/0268116 A1 | 10/2012 | Zhu |

\* cited by examiner

MAGNETIC RESONANCE IMAGING SYSTEM WITHOUT INTEGRATED BODY COIL

CROSS REFERENCE TO RELATED APPLICATIONS

This application is a U.S. national phase application of International Application No. PCT/EP2014/067463, filed on Aug. 15, 2014, which claims the benefit of EP Application Serial No. 13180557.4 filed on Aug. 15, 2013 and is incorporated herein by reference.

FIELD OF THE INVENTION

The invention relates to a system in the field of magnetic resonance imaging and more specifically to transmit and/or receive of RF signals.

BACKGROUND OF THE INVENTION

U.S. Pat. No. 6,529,004B1 deals with a radiofrequency (RF) coil for transmitting RF signals. The RF coil is secured to the patient support so as to be movable with the patient support along the bore. At least part of the RF coil is laterally displaceable with respect to the bore to permit imaging of different regions of the body. The width of the central section of the RF coil may be variable in a lateral direction to accommodate patients of different size.

SUMMARY OF THE INVENTION

It is an object of the invention to find a system for transmitting and/or receiving RF signals which can be adapted to different object sizes with more flexibility.

This object is achieved by a transmit and/or receive coil assembly comprising
a first exchangeable part configured for transmitting and/or receiving RF signals,
a second exchangeable part configured for transmitting and/or receiving RF signals and
a permanent part configured for transmitting and/or receiving RF signals; Wherein
the first exchangeable part is exchangeable with the second exchangeable part and wherein
the first exchangeable part has a different size than the second exchangeable part and wherein
the first and second exchangeable part are configured to cooperate with the permanent part during magnetic resonance imaging in such a way that
an RF field generated by the permanent part in combination with the first or second exchangeable part covers a volume of interest of an object to be scanned and/or
a spatial sensitivity to receiving RF signals of the permanent part in combination with the first or second exchangeable part covers the volume of interest of the object to be scanned.

It is an insight of the invention that more flexibility is desirable to adjust the RF coil to the individual object. The invention provides a transmit and/or receive coil assembly comprising a first and second exchangeable part configured for transmitting and/or receiving RF signals. The exchangeable parts are exchangeable with each other and configured to cooperate with a permanent part of the transmit and/or receive coil assembly during magnetic resonance imaging in order to generate an RF (or B1+) field that covers a volume of interest of the object to be scanned and/or to receive magnetic resonance signals from the volume of interest of the object. When the first or second exchangeable part is positioned relative to the permanent part in such a way that the combination is suitable for magnetic resonance imaging, the resulting combination is here called "coil combination". Regarding the B1+ field it is important that a sufficiently high amplitude is reached in a volume of interest and that the transmit field is sufficiently homogeneous in order to obtain a clinically useful image quality. For a receive coil combination, it is of importance that its spatial sensitivity to RF signals covers the volume of interest and is sufficient for use in magnetic resonance imaging.

Increasing the bore size (wide bore system) of MRI systems by scaling the MRI system results in increasing component cost, ineffective body coils and the need for large RF power, especially for multi-transmit systems. Local transmit and receive coils can reach high fields needed for clinical applications, but only locally. Often RF body coils are optimized to be as thin as possible. This enables scanning of bigger objects (e.g. patients, animals, body parts) and reduces the risk of claustrophobia. However, for the RF body coil a reduction of thickness means a reduction of efficiency for transmission and reception. Since these coils and wide-bore systems are designed to fit larger objects, RF transmit and receive efficiency is mainly reduced in normal and small-sized objects. To solve this issue, the transmit and/or receive coil assembly of the invention may be used to replace an integrated body coil in the MRI system.

Because the sizes of the proposed first and second exchangeable part differ, the size of the coil combination can be altered based on the size of an object to be scanned. In this way the B1+ efficiency and/or a spatial sensitivity of a coil is optimized for objects of different sizes.

Because the RF coil assembly provides two exchangeable parts, more flexibility exists to adjust the coil combination to the size of the individual object. When the RF coil assembly is configured as a volume resonator, costs of the extra (exchangeable) coil part can be justified, since in this way one single MRI system can be optimized for both small and large patients, for which otherwise two MRI systems with two different bore sizes would be needed.

In an embodiment of the invention, the first and/or second exchangeable part is rigid. A rigid shape can be designed in such a way that the first and/or second exchangeable part does not rest on or touch the object to be scanned when used for scanning the object. Another advantage of a rigid shape is that a well-defined shape of the coil makes it easier to make a reliable estimation of the SAR delivered to the object to be scanned by a certain imaging sequence.

In one of the embodiments of the invention the permanent and first and/or exchangeable second part comprises at least two axially separate portions, which are parallel to a longitudinal axis of the coil combination. This is advantageous, since in this way during scanning a smaller or larger field-of-view can be used, by adjusting the number of portions used during scanning the object.

In one embodiment of the invention the permanent part of the transmit and/or receive coil assembly is integrated in an object support suitable to fit in the MRI system. Preferably, RF signals are transmitted optically or via shielded capacitive or inductive RF transformers. In this way, the first and second exchangeable part are made light-weight, so that they can be easily moved, positioned and/or removed by a nurse/assistant. Therefore this embodiment will make coil handling easier. Furthermore, this embodiment may improve workflow. According to one aspect of the invention, the first and second exchangeable part are detachably mountable to the permanent part or the object support. According to another aspect of the invention the first and second exchangeable part can be located contactless over the permanent part. According to another aspect of the invention the first and second exchangeable part can be disposable. According to another aspect of the invention the first and second exchangeable part is light-weight (up to about 50% reduction in weight) as part of driver, detection and preamplifier electronic is located in permanent part of the transmit and receive coil assembly.

The transmit and/or receive coil assembly of the invention can be combined with an MRI system. This could be an MRI system without an integrated body coil. When used in an MRI system without integrated body coil, the coil combination preferably is a volume resonator and could be configured to replace the integrated body coil. When replacing the integrated body coil, the volume resonator will substantially cover an examination zone created by a main magnet inside a bore of the MRI system. Substantial coverage is creating a field of view in the order of at least 40×40×40 $cm^3$, which is located in the examination zone. The first and second exchangeable part of the coil combination are configured to be detachably mountable to the MRI system. In this way the MRI system can be adapted to objects of different sizes.

The transmit and/or receive coil assembly of the invention can be combined with another local receive coil assembly. The local receive coil assembly MRI system can be flexible and directly be located on the subject.

In one embodiment of the invention at least one of the permanent part or first or second exchangeable part of the transmit and/or receive coil assembly is translatable in the longitudinal direction relative to the object support and the MRI system when connected to the MRI system or object support. Translation in longitudinal direction may be electromechanically controlled by means of an electrical drive and electromechanical control system. Motion of at least one of the permanent part or first or second exchangeable part of the transmit and/or receive coil assembly could be initiated by a user for example by pushing a button, using a touch screen, joy stick, keyboard in the examination or control room. This embodiment could be used in the following way: the first or second exchangeable part can be parked in the bore of the MRI system, when the object is positioned at the object support. After object preparation prior to an MRI exam is finished, the first or second exchangeable part can be slid over the object. This may increase object comfort, because the object is not aware of the presence of the first or second exchangeable part.

This embodiment is also advantageous, when combined with a transmit and/or receive coil assembly. With the transmit and/or receive coil assembly, it is possible to switch between a smaller and a larger FOV, by using less or more axial coil parts. It may be beneficial to translate the permanent or first/second exchangeable part in the longitudinal direction relative to the MRI system and the object support. In this way can be prevented that the coils are positioned in such a way that when going from a larger to a smaller FOV, the edge of the smaller FOV will fall within a volume of interest. The center of the coil parts used for scanning the smaller FOV can be translated to cover a new volume of interest or can be translated to the isocenter of the main magnet of the MRI system.

In another embodiment of the invention the transmit and/or receive coil assembly can be used in combination with an MRI guided therapy system comprising a radiation module (like e.g. an MRI-Linac) configured for emitting therapeutic radiation (e.g. X-ray, electrons). The MRI system may be an MRI system without an integrated body coil. This embodiment is advantageous, because radiation from the radiation source will most likely ultimately destroy the coils in the MRI system. When using the coil assembly of the invention instead of an integrated body coil, coil replacement can much easier be performed, making maintenance of the MRI system cheaper.

These and other aspects of the invention will be apparent from and elucidated with reference to the embodiments described hereinafter.

DETAILED DESCRIPTION OF THE INVENTION

Figure 1:
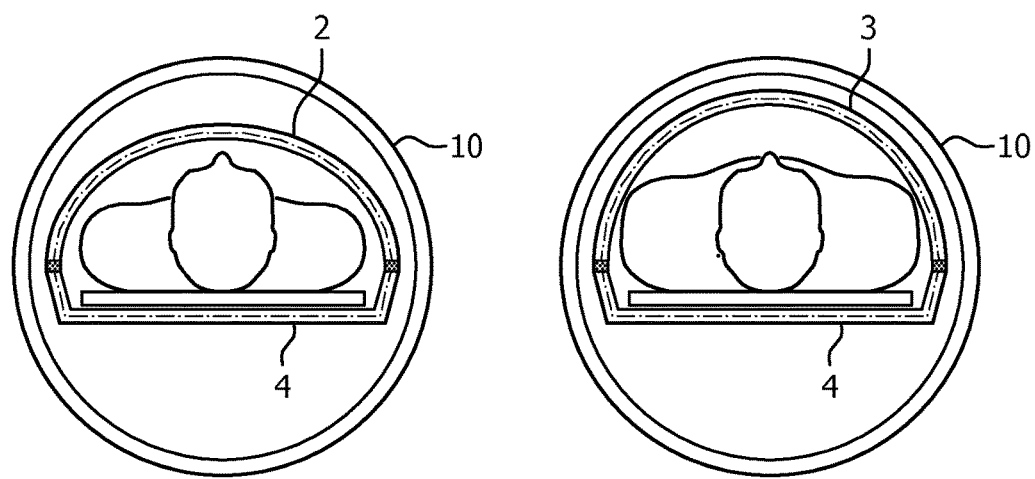
FIG. 1 illustrates diagrammatically an MRI system using the transmit/receive coil assembly of the invention.

FIG. 1 illustrates diagrammatically an MRI system using the transmit/receive coil assembly of the invention. The transmit/receive coil assembly comprises a first (2) and second (3) exchangeable part. In these examples the first and second exchangeable part are positioned on the anterior side of the object to be scanned. The first and second exchangeable part are configured for transmitting and/or receiving RF signals and are different in size. By combining either the first (2) or the second (3) exchangeable part with the permanent part (4, in this image located on posterior side of the object to be scanned) one can adapt the coil combination to fit different object sizes. The coil combination is tuned to be resonant at the Larmor frequency of nuclei of interest by adjusting the values of capacitors. In this way the efficiency for transmission and/or reception can be optimized for patients of different sizes.

The mechanic interconnection is preferably rigid so that it does not change during scanning and by moderate movement of the patient. Also the electromagnetic connection can be designed as one or more plugs connected by mounting first (2) or second exchangeable part (3) onto.

However, a direct (galvanic) electromagnetic connection between the permanent part (4) and first (2) or second exchangeable part (3) is not required. RF transmit signals could be coupled inductively via feeding coils integrated into permanent part (4), and/or shielded capacitive or inductive RF transformers. When having first (2) or second exchangeable part (3) equipped with independent driving channels (number of transmit channels>1), the parts could also be controlled independently to obtain a desired RF field.

The same means can be applied for the MR receive signals acquired by the first (2) or second exchangeable part (3), but here also an optical signal transport can be realized from first (2) or second exchangeable part (3) to permanent part (4) and from there to the spectrometer.

Using the methods without galvanic connection between the first and/or second exchangeable part reduces weight, makes it more easy to handle and increases reliability of the parts involved.

As shown in FIG. 1, in an embodiment of the invention the first (2) and/or second exchangeable part (3) is rigid. As a result, these exchangeable parts do not necessarily touch the object to be scanned. Furthermore, a well-defined shape makes it easier to make a reliable estimation of the SAR delivered to the object to be scanned by a certain imaging sequence. The SAR depends on tissue's electrical conductivity and density, together with the total electric field. In order to obtain an accurate estimate of the electric field and thereby of the SAR, knowledge of the position of the transmit coils is important. By having a volume coil better fitting to the patient, the SAR prediction of the scan software does not need to consider very high safety margins considering coil to patient variability. This enables to predict the SAR more precisely, allowing to apply more RF power to certain patients where the safety margin formerly was overestimated.

Figure 2:
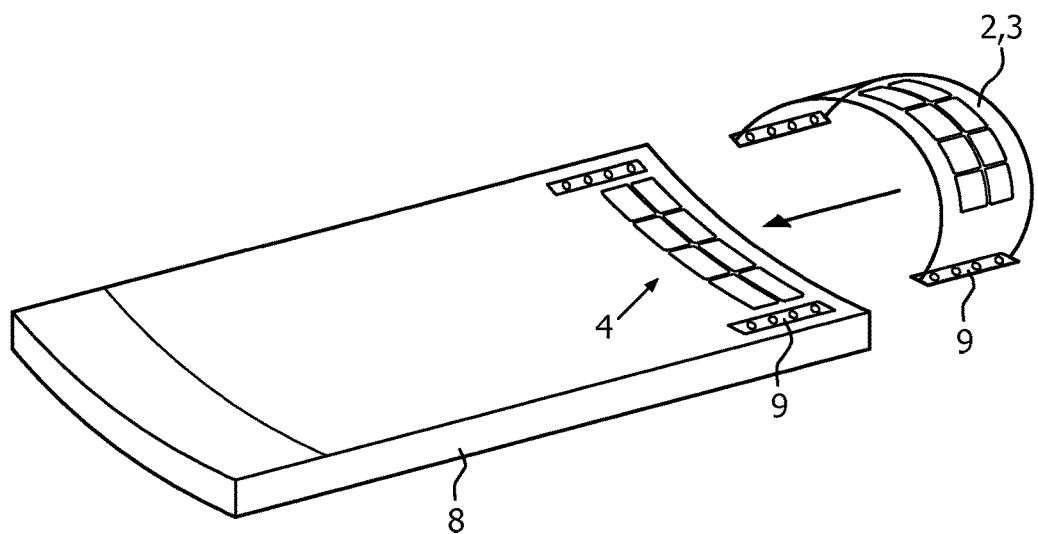
FIG. 2 illustrates diagrammatically an object support, in which the permanent part of the transmit and/or receive coil assembly is integrated.

FIG. 2 illustrates diagrammatically an object support (8), in which the permanent part (4) of the transmit and/or receive coil assembly is integrated.

The first (2) and second exchangeable (3) part could be configured such that they do not need to be connected to the permanent part (4) for scanning an object. For example, the first (2) or second exchangeable (3) part could be positioned above the patient, e.g. by hanging it in the bore.

The first (2) and second exchangeable (3) part could also be configured to be detachably mountable to the object support. Mechanical fixation points (9) could be used to keep the first and/or second exchangeable part in position.

FIG. 3 illustrates diagrammatically how the transmit/receive coil assembly can be combined with an MRI system. The transmit/receive coil assembly could be combined with an MRI system with or without an integrated body coil. FIG. 3 shows an example wherein the transmit and/or receive coil assembly is combined with an MRI system without integrated body coil. The MRI system comprises a main magnet (16). The main magnet (16) creates an examination zone (22) in the MRI system by aligning spins with the main magnetic field. The MRI system further comprises a gradient coil (12). The coil combination (2 or 3, 4) is a volume resonator and replaces the integrated body coil. The exchangeable parts (2,3) are detachably mountable to the MRI system. Also the permanent part could be detachably mountable to the MRI system.

Figure 3A:
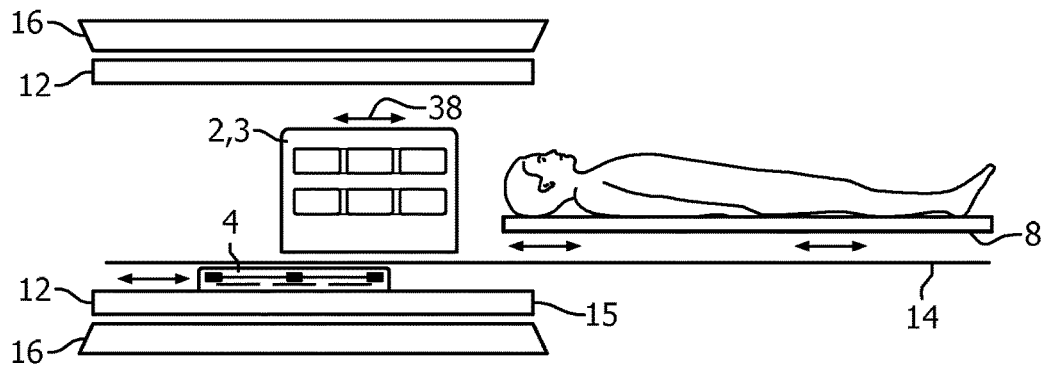
FIG. 3 illustrates diagrammatically how the transmit/receive coil assembly can be combined with an MRI system without an integrated body coil.
Figure 3B:
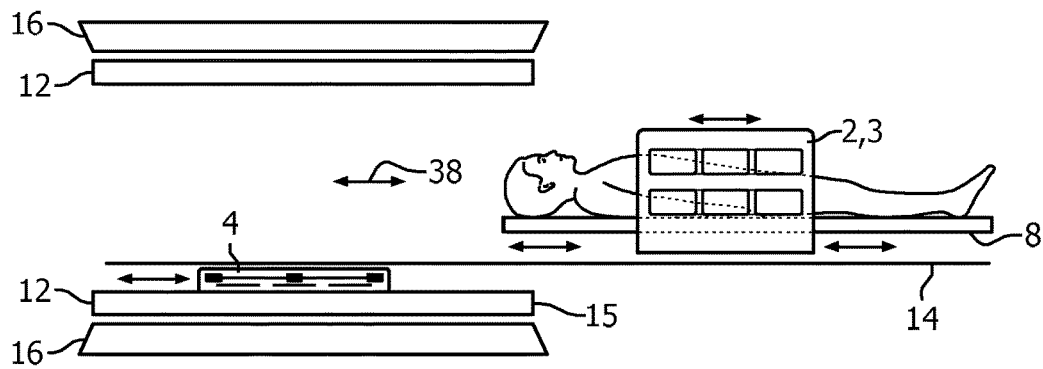
Figure 3C:
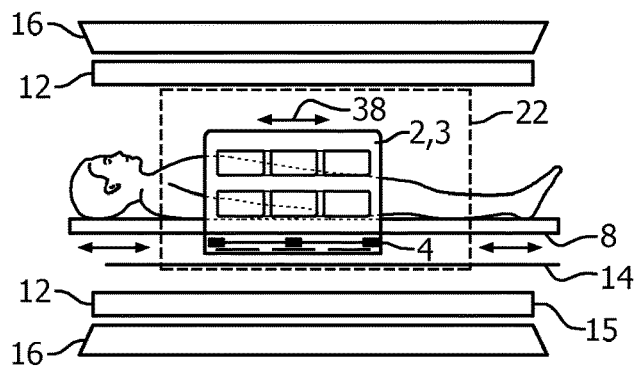

The MRI system comprises an object support (8) to position the object to be scanned. At least one of the first exchangeable part (2), second exchangeable part (3) or permanent part (4) is translatable in the longitudinal direction (38) relative to the magnetic resonance imaging system and the object support (8) after connection to the magnetic resonance imaging system or object support (8). A translation of one or more of these coil parts in lateral direction could also be possible. The MRI system comprises a slide (14) to move the permanent (4) and/or first (2) or second exchangeable part (3) in and out the scanner. The permanent (4) and/or first (2) or second exchangeable part (3) could also be moved in and out the MRI system in other ways, e.g. by means of runners, guides, rails etc. Movement of the permanent (4) and/or first (2) or second exchangeable part (3) could be performed manually or electromechanically. Electromechanical movement could for example be initiated by means of pushing a button, using a joystick or keyboard or by using a graphical user interface (15) in the examination or control room. The permanent part (4) of the transmit/receive coil assembly could be integrated in the MRI system and is either combined with the first exchangeable part (2) or the second exchangeable part (3). The coil combination is configured to be used for magnetic resonance imaging and suitable for transmitting and/or receiving RF signals Possibly the MRI system can be used in the following way. If a patient enters the examination room the permanent part and first or second exchangeable part are positioned in the bore of the MRI system (FIG. 3a). In this way the patient does not directly see the coil combination (permanent part and/or first or second exchangeable part), which may improve patient comfort. When the patient is positioned on the object support at least one of the permanent or first or second exchangeable part is moved under or over the patient and positioned in the desired way (FIG. 3b). Then the object support with at least one of the permanent part or first or second exchangeable part could be moved inside the scanner (FIG. 3c). Prior to imaging the patient, the permanent and first or second exchangeable part are tuned to transmit and/or receive RF signals to and/or from the patient.

Figure 4:
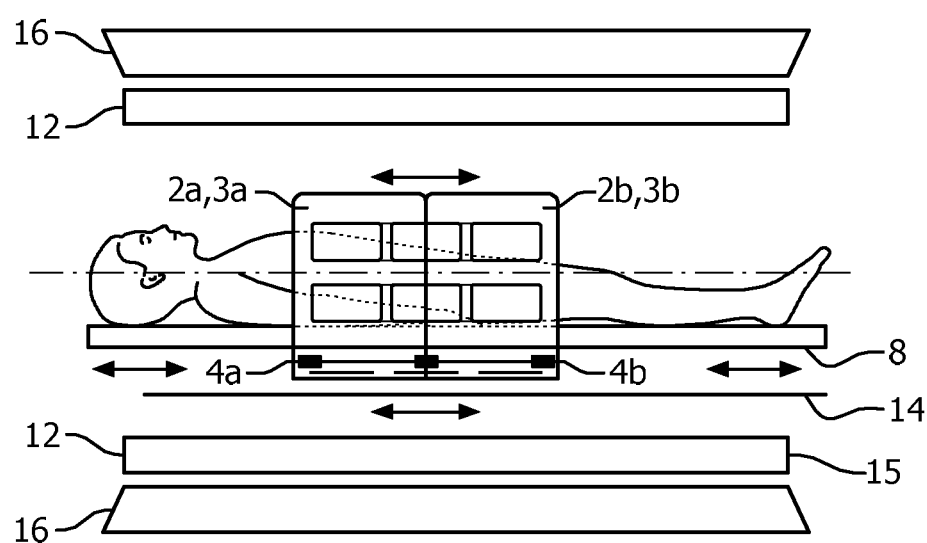
FIG. 4 illustrates diagrammatically an transmit and/or receive assembly wherein the permanent part and the first and/or second exchangeable part comprise at least two axially separate portions

FIG. 4 illustrates diagrammatically a transmit and/or receive assembly wherein the permanent part and the first and/or second exchangeable part comprise at least two axially separate portions ($2a,2b,3a,3b,4a,4b$). The separate portions ($2a,2b,3a,3b,4a,4b$) are separate parallel to the longitudinal axis (28) of the coil combination, which is in this image in the cranial-caudal direction. This embodiment can be used to switch during an MRI exam to a FOV of a different size. The coil combination can be translated to better align with a volume of interest in the object and with the isocenter of the MRI system. After movement, the coils may need to be tuned again and new MRI preparation scans may be needed.

In another embodiment of the invention the transmit and/or receive coil assembly can be used in combination with an MRI system comprising a radiation module, like e.g. an MRI-Linac. The MRI system may be an MRI system without an integrated body coil. The coil combination could easily be moved in and out the MRI system, which makes replacement of a coil or its components easier.

Whilst the invention has been illustrated and described in detail in the drawings and foregoing description, such illustrations and description are to be considered illustrative or exemplary and not restrictive; the invention is not limited to the disclosed embodiments and can be used for RF transmit and/or receive within the field of magnetic resonance imaging.

The invention claimed is:

1. A magnetic resonance imaging system comprising a patient support and a main magnet, wherein the main magnet creates an examination zone in the magnetic resonance system by alignment of spins with a main magnetic field wherein the magnetic resonance system further comprises a body coil assembly, wherein the body coil assembly comprises:
   a first exchangeable body coil part configured for at least one of transmitting and receiving RF signals;
   a second exchangeable body coil part, exchangeable with the first body coil exchangeable part and configured for at least one of transmitting and receiving RF signals; wherein
   the first and second exchangeable parts are each individually detachably mountable to the patient support and are rigid and configured to extend over a body portion of a patient supported on the patient support;

a permanent body coil part configured for at least one of transmitting and receiving RF signals and configured to form a volume resonator when combined with the first or second exchangeable body coil part such that by cooperation of the permanent body coil part and the first or second exchangeable body coil part, the RF field generated by the volume resonator substantially covers the examination zone; wherein the first exchangeable part and the second exchangeable part differ in size in order to alter the size of the volume resonator to accommodate patients of different sizes.

2. The magnetic resonance imaging system as set forth in claim 1, wherein the body coil assembly has a longitudinal axis, and wherein the permanent and first or second exchangeable body coil parts comprise at least two axial separate portions, which are parallel to the longitudinal axis when the permanent part is combined with the first or second exchangeable part, and further including a button, joystick, keyboard, or a graphical user interface configured for electromechanically moving the first and/or second exchangeable body coil part longitudinally along the patient support.

3. A magnetic resonance imaging system comprising:
a cylindrical housing which defines an annular bore;
a main magnet and a gradient magnet disposed within the cylindrical housing, the main magnet and the gradient magnet defining a magnetic resonance examination zone in the annular bore, the housing being without an integrated or built-in body RF transmit coil;
a patient support configured to transport a patient into and out of the examination zone;
a body transmit coil assembly including:
  a permanent part of the body transmit coil assembly integrated in the patient support,
  a first exchangeable rigid RF transmit coil part configured to be supported by the patient support, arc over a patient supported on the patient support, and be electrically coupled to the permanent part, wherein the permanent part and the first exchangeable part form a volume resonator configured to, when the patient support is in the bore, transmit RF signals into the examination region, and
  a second exchangeable rigid RF transmit coil part configured to be, when the first exchangeable rigid RF transmit coil part is removed, supported by the patient support, arc over a patient supported on the patient support, and be electrically coupled to the permanent part, wherein the permanent part and the second exchangeable part form a volume resonator configured to, when the patient support is in the bore, transmit RF signals into the examination region.

4. The magnetic resonance imaging system set forth in claim 1, wherein the permanent body coil part is integrated into the patient support and the first and second body coil parts are configured to be detachably mountable to the permanent part integrated into the patient support.

5. The magnetic resonance imaging system set forth in claim 1, wherein the permanent body coil part is mounted in a bore of the magnetic resonance system and is configured to translate in the longitudinal direction relative to the magnetic resonance imaging system independently of the patient support and the first or second exchangeable body part.

6. The magnetic resonance imaging system set forth in claim 1, wherein at least part of the body coil assembly is configured for electromechanical translation in longitudinal direction relative to the magnetic resonance imaging system and the patient support.

7. The magnetic resonance imaging guided therapy system comprising a magnetic resonance system as set forth in claim 1 comprising a radiation module configured for emitting therapeutic radiation.

8. The magnetic resonance imaging system as set forth in claim 1 without an integrated or built-in body coil.

9. The magnetic resonance imaging system as set forth in claim 3, wherein the body coil assembly is also a receive coil assembly.

10. The magnetic resonance imaging system as set forth in claim 1, wherein the first and second body coil parts are of different sizes to accommodate patients of different girths.

11. A magnetic resonance imaging system, comprising:
a cylindrical housing which defines an annular bore;
a main magnet and a gradient magnet disposed within the cylindrical housing, the main magnet and the gradient magnet defining a magnetic resonance examination zone in the annular bore, the housing being without an integrated or built-in body RF transmit coil;
a patient support configured to transport a patient into and out of the examination zone;
a body coil assembly including:
  a permanent part of the body coil assembly being mounted in the annular bore adjacent the magnetic resonance examination zone separate from the patient support and to the cylindrical housing,
  a first exchangeable rigid RF body coil part configured to be supported by the patient support, arc over a body portion of a patient supported on the patient support, and be electrically coupled to the permanent part when the first exchangeable rigid RF body coil part is disposed adjacent permanent part, wherein the permanent part and the first exchangeable part form a volume resonator configured to, when the patient support is in the bore, transmit and/or receive RF signals from the examination region, and
  a second exchangeable rigid RF body coil part configured to be supported, when the first exchangeable rigid RF body coil part is removed, by the patient support, arc over the body portion of the patient supported on the patient support, and be electrically coupled to the permanent part when the second exchangeable rigid RF body coil part is disposed adjacent permanent part, wherein the permanent part and the second exchangeable part form a volume resonator configured to, when the patient support is in the bore, transmit and/or RF signals into/from the examination region,
  wherein the first exchangeable body coil part is larger than the second exchangeable body coil part such that the first exchangeable body coil part is configured for imaging larger patients and the second body coil part is configured for imaging smaller patients.

12. The magnetic resonance imaging system as set forth in claim 11, wherein the one of the first and second exchangeable rigid RF transmit coil parts which is supported by the patient support is configured to be moved axially along the patient support.

13. The magnetic resonance imaging system as set forth in claim 1, wherein the patient support is configured to move the patient longitudinally into and out of the examination zone and the first and second exchangeable body coil parts have different widths in a lateral direction to accommodate patients of a different size.

14. The magnetic resonance imaging system as set forth in claim 3, wherein the patient support is configured to move the patient longitudinally into and out of the examination zone and the first and second exchangeable rigid RF transmit parts have different widths in a lateral direction to accommodate patients of a different size.

15. The magnetic resonance imaging system as set forth in claim 3, wherein the body transmit coil assembly has a longitudinal axis, and wherein the first or second exchangeable body coil parts comprise at least two axial separate portions, which are disposed parallel to the longitudinal axis and further including a button, joystick, keyboard, or a graphical user interface configured for electromechanically moving at least one of the at least two axial separate portions of the first and/or second exchangeable body coil part longitudinally along the patient support.

16. The magnetic resonance imaging system as set forth in claim 11, wherein the patient support is configured to move the patient longitudinally into and out of the examination zone and the first and second exchangeable parts have different widths in a lateral direction to accommodate patients of a different size.

17. The magnetic resonance imaging system as set forth in claim 11, wherein the body coil assembly has a longitudinal axis, and wherein the first or second exchangeable body coil part is disposed parallel to the longitudinal axis when the permanent part is combined with the first or second exchangeable part, and further including a button, joystick, keyboard, or a graphical user interface configured for electromechanically moving the first and/or second exchangeable body coil part longitudinally along the patient support.

* * * * *